(12) United States Patent
Lim et al.

(10) Patent No.: US 11,857,773 B2
(45) Date of Patent: Jan. 2, 2024

(54) SYRINGE SAFETY CAP AND SAFETY SYRINGE INCLUDING THE SAME

(71) Applicant: DAEWOONG PHARMACEUTICAL CO., LTD., Gyeonggi-do (KR)

(72) Inventors: Duck Soo Lim, Gyeonggi-do (KR); Jun Sik Kim, Gyeonggi-do (KR); Ji Young Oh, Gyeonggi-do (KR); In Ho Kim, Gyeonggi-do (KR)

(73) Assignee: DAEWOONG PHARMACEUTICAL CO., LTD., Gyeonggi-do (KR)

( * ) Notice: Subject to any disclaimer, the term of this patent is extended or adjusted under 35 U.S.C. 154(b) by 309 days.

(21) Appl. No.: 17/297,513

(22) PCT Filed: Nov. 27, 2018

(86) PCT No.: PCT/KR2018/014741
§ 371 (c)(1),
(2) Date: May 27, 2021

(87) PCT Pub. No.: WO2020/111295
PCT Pub. Date: Jun. 4, 2020

(65) Prior Publication Data
US 2022/0008662 A1 Jan. 13, 2022

(51) Int. Cl.
*A61M 5/32* (2006.01)
*A61M 5/50* (2006.01)

(52) U.S. Cl.
CPC ........ *A61M 5/3216* (2013.01); *A61M 5/3276* (2013.01); *A61M 5/50* (2013.01);
(Continued)

(58) Field of Classification Search
CPC .... A61M 5/3216; A61M 5/3276; A61M 5/50; A61M 5/3219; A61M 5/321;
(Continued)

(56) References Cited

U.S. PATENT DOCUMENTS 5,405,332 A * 4/1995 Opalek ............... A61M 5/3216
604/263
9,662,455 B2 5/2017 Wickham
(Continued)

FOREIGN PATENT DOCUMENTS

EP 0654281 B1 7/2001
JP 2016137230 A 8/2016

*Primary Examiner* — Nathan R Price
*Assistant Examiner* — Sarah Dympna Grasmeder
(74) *Attorney, Agent, or Firm* — Hammer & Associates, P.C.

(57) ABSTRACT

The present disclosure relates to a syringe safety cap and a safety syringe including the same. One aspect of the present disclosure provides a syringe safety cap including a base portion having a mounting portion to be mounted on a cylinder of a syringe, a link portion rotatably connected to the base portion, a first elastic portion configured to provide a rotational force so that the link portion rotates with respect to the base portion, a safety cover portion rotatably connected to the link portion, detachably fixed to the base portion, and configured to, when detached from the base portion and rotating, surround an injection needle of the syringe, and a second elastic portion configured to provide a rotational force so that the safety cover portion rotates with respect to the link portion.

17 Claims, 11 Drawing Sheets

(52) U.S. Cl.
CPC .............. *A61M 2005/3217* (2013.01); *A61M 2205/273* (2013.01)

(58) Field of Classification Search
CPC ........ A61M 5/3275; A61M 2005/3217; A61M 2205/273
See application file for complete search history.

(56) References Cited

U.S. PATENT DOCUMENTS

| | | |
|---|---|---|
| 9,764,097 B2 | 9/2017 | Perot et al. |
| 11,318,258 B2* | 5/2022 | Okajima .............. A61M 5/3275 |
| 2003/0181861 A1* | 9/2003 | Wilkinson ........... A61M 5/3216 604/192 |
| 2003/0212369 A1* | 11/2003 | Kobayashi .......... A61M 5/3216 604/197 |
| 2008/0208138 A1 | 8/2008 | Lim et al. |
| 2008/0306451 A1* | 12/2008 | Woehr ................. A61M 5/3216 604/198 |
| 2009/0259201 A1* | 10/2009 | Hwang ............ A61B 5/150648 604/263 |
| 2016/0317755 A1* | 11/2016 | Wang .................. A61M 5/3216 |

* cited by examiner

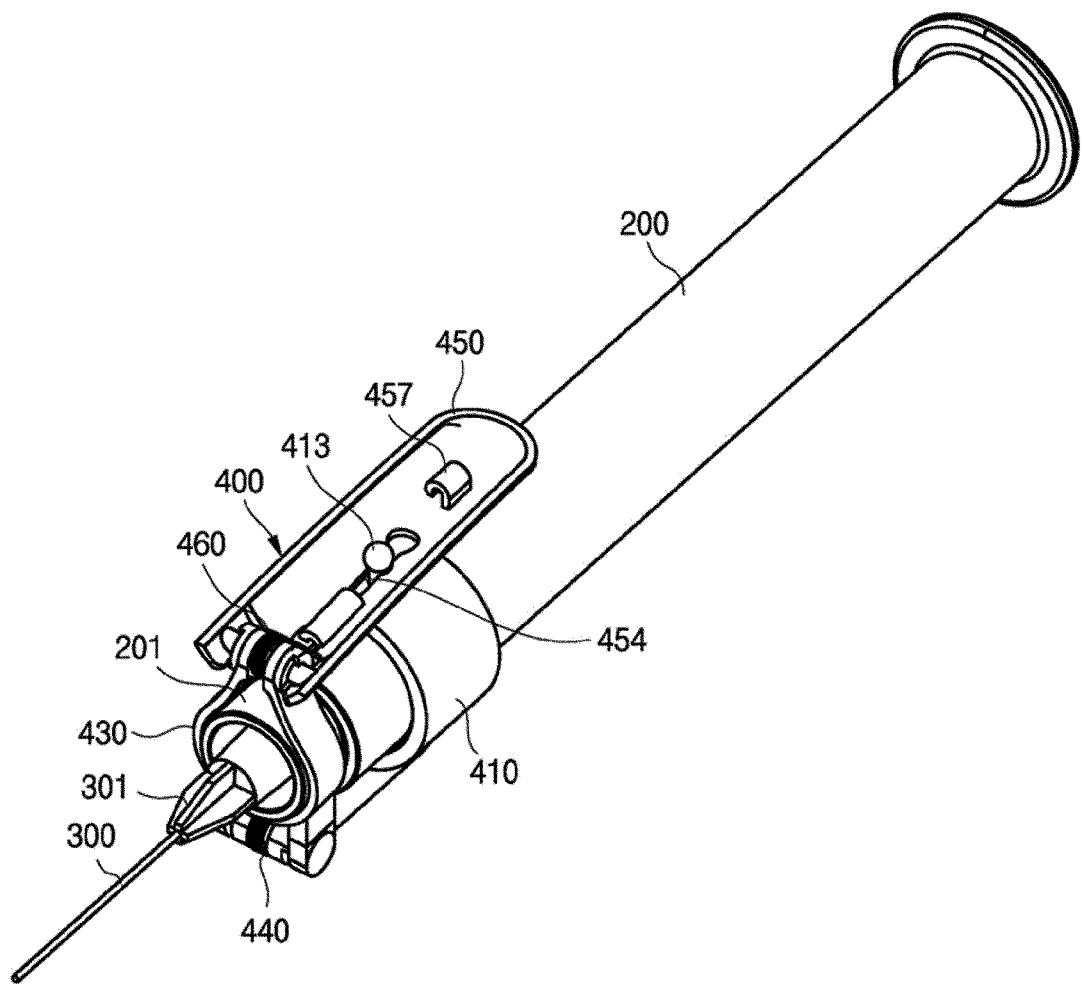
[FIG. 1]

[FIG. 2]
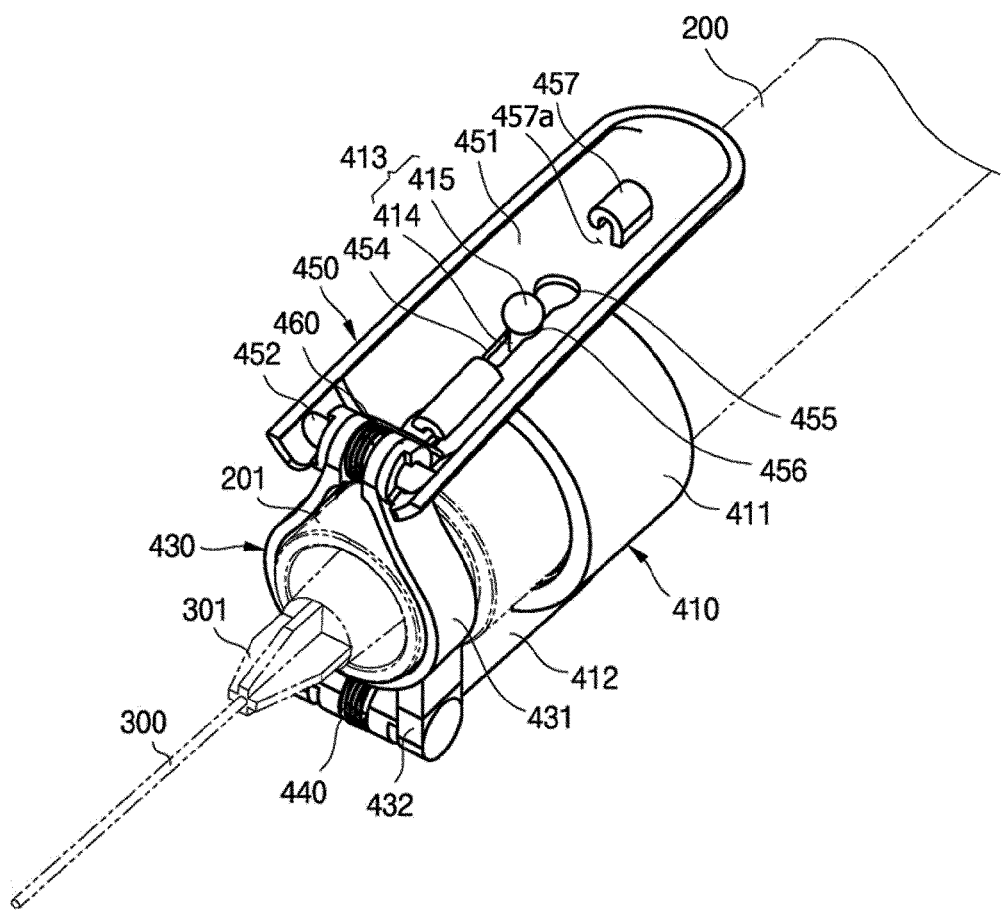

[FIG. 3]
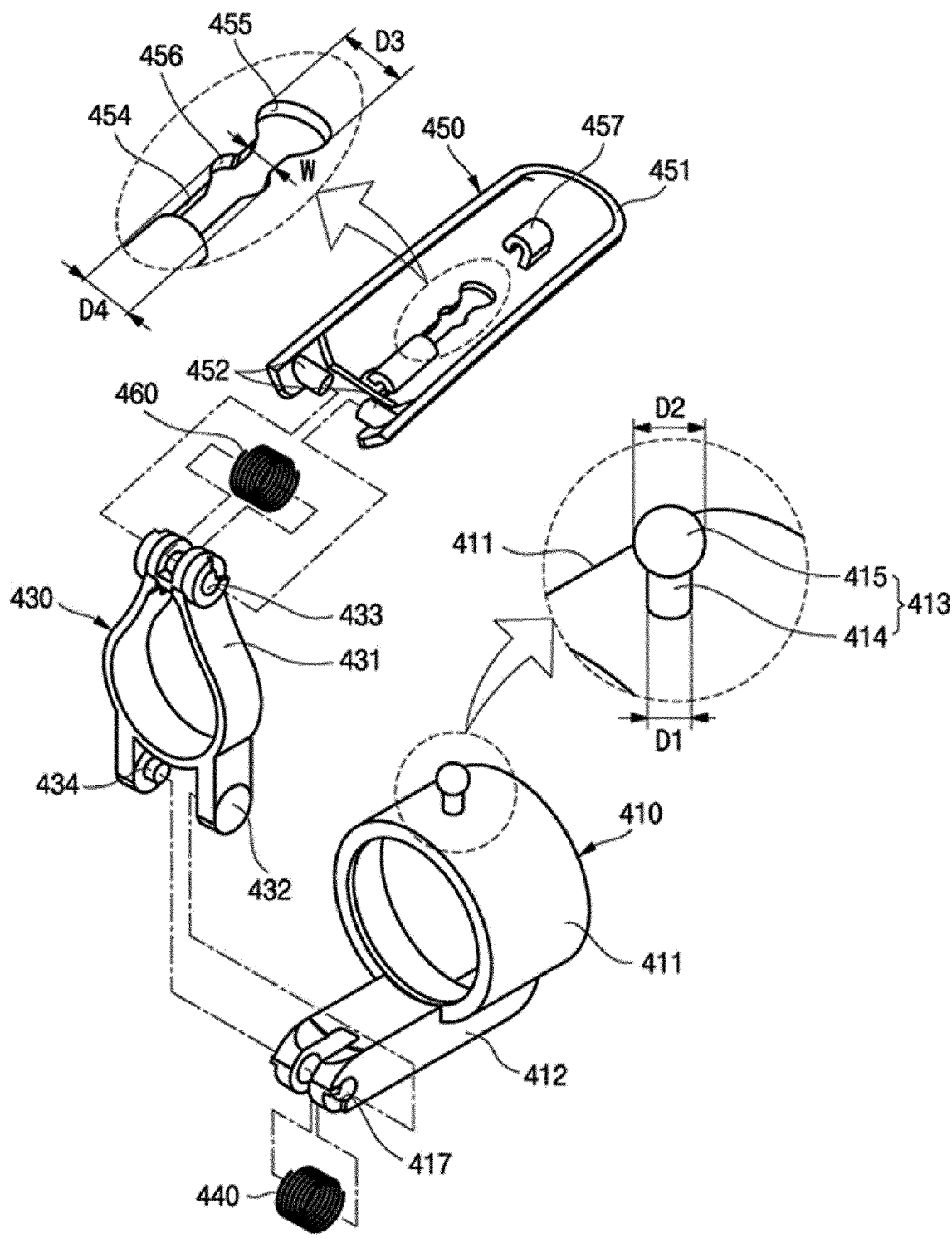

[FIG. 4]
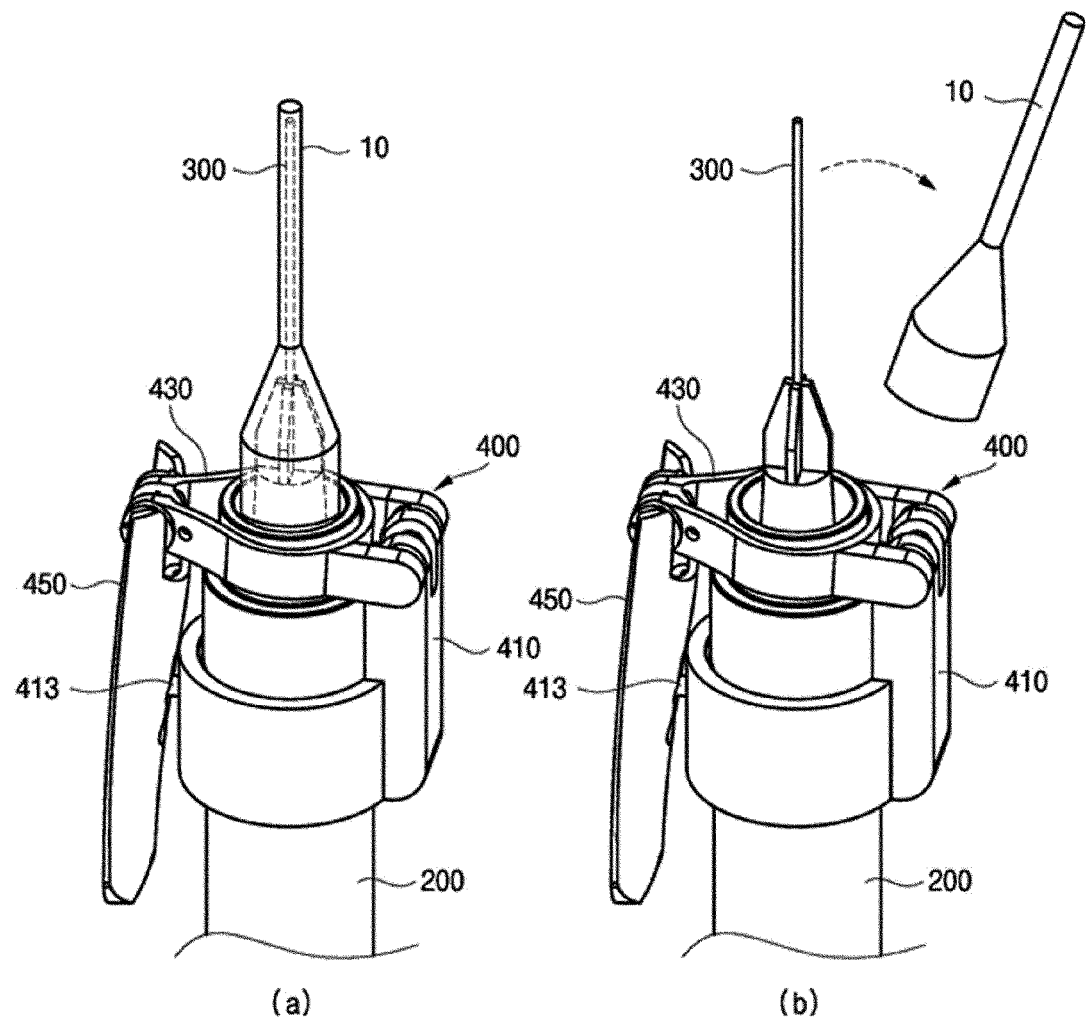

[FIG. 5]
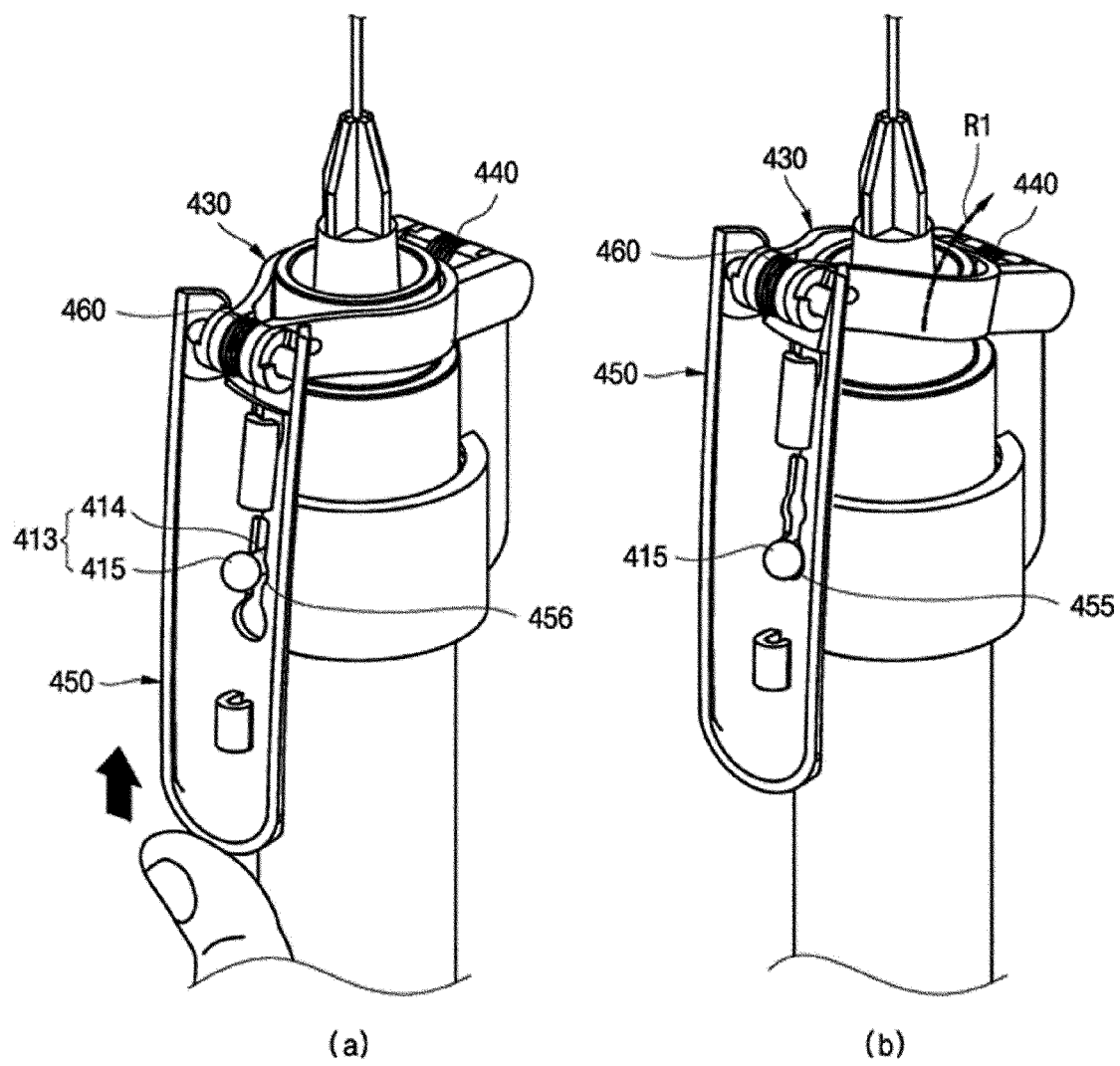

[FIG. 6]
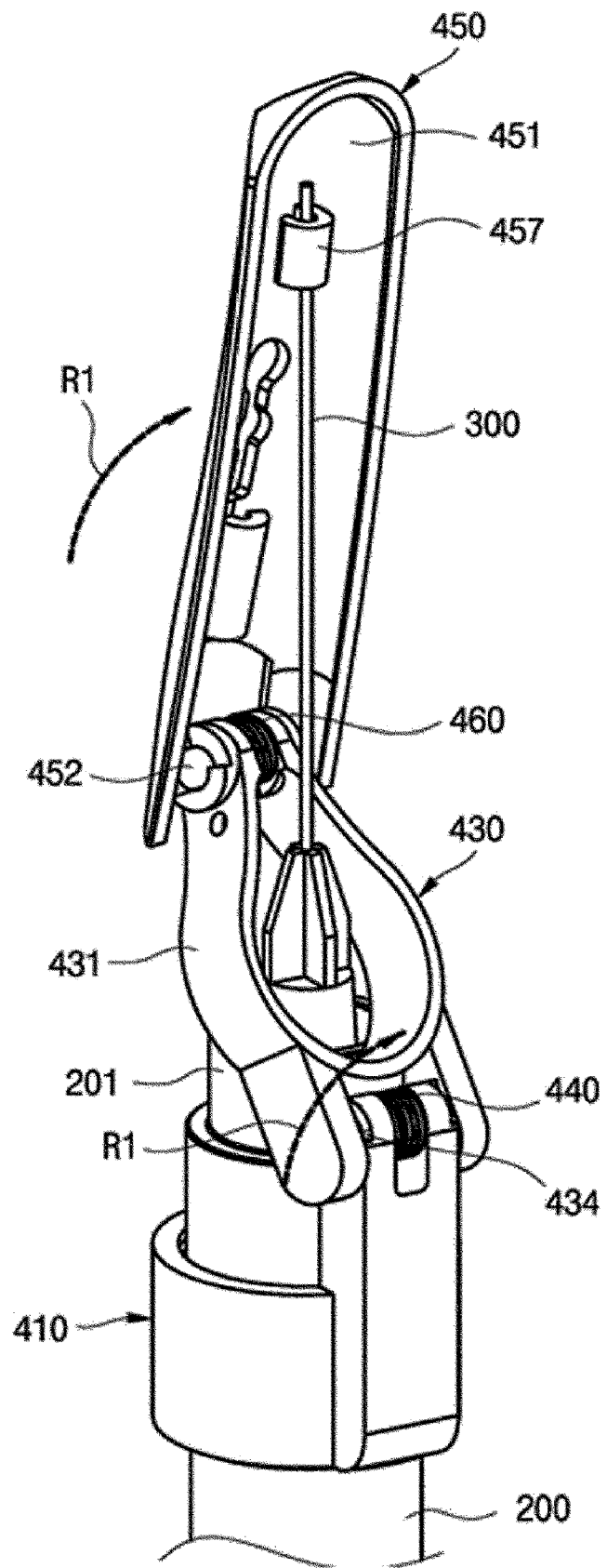

[FIG. 7]
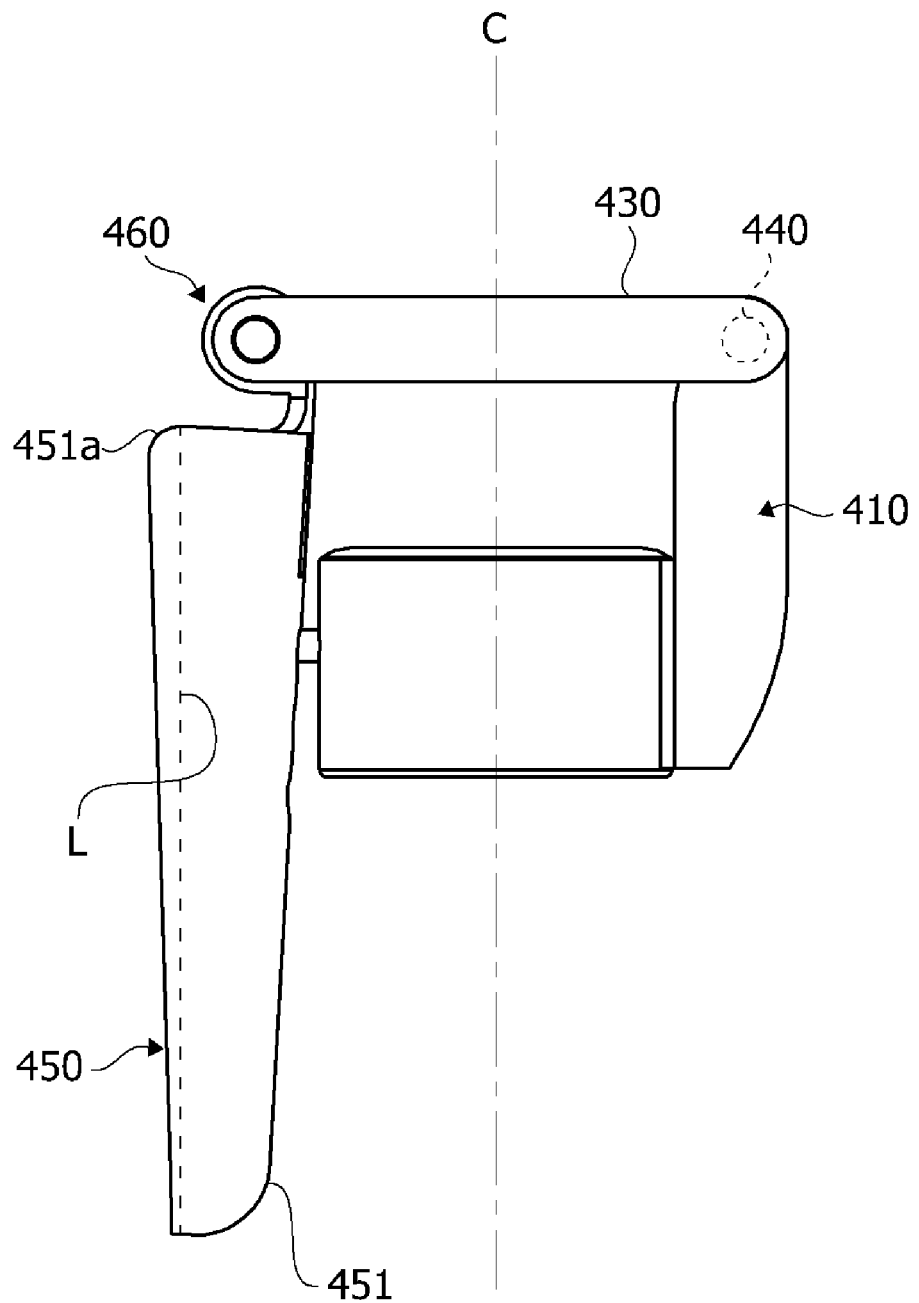

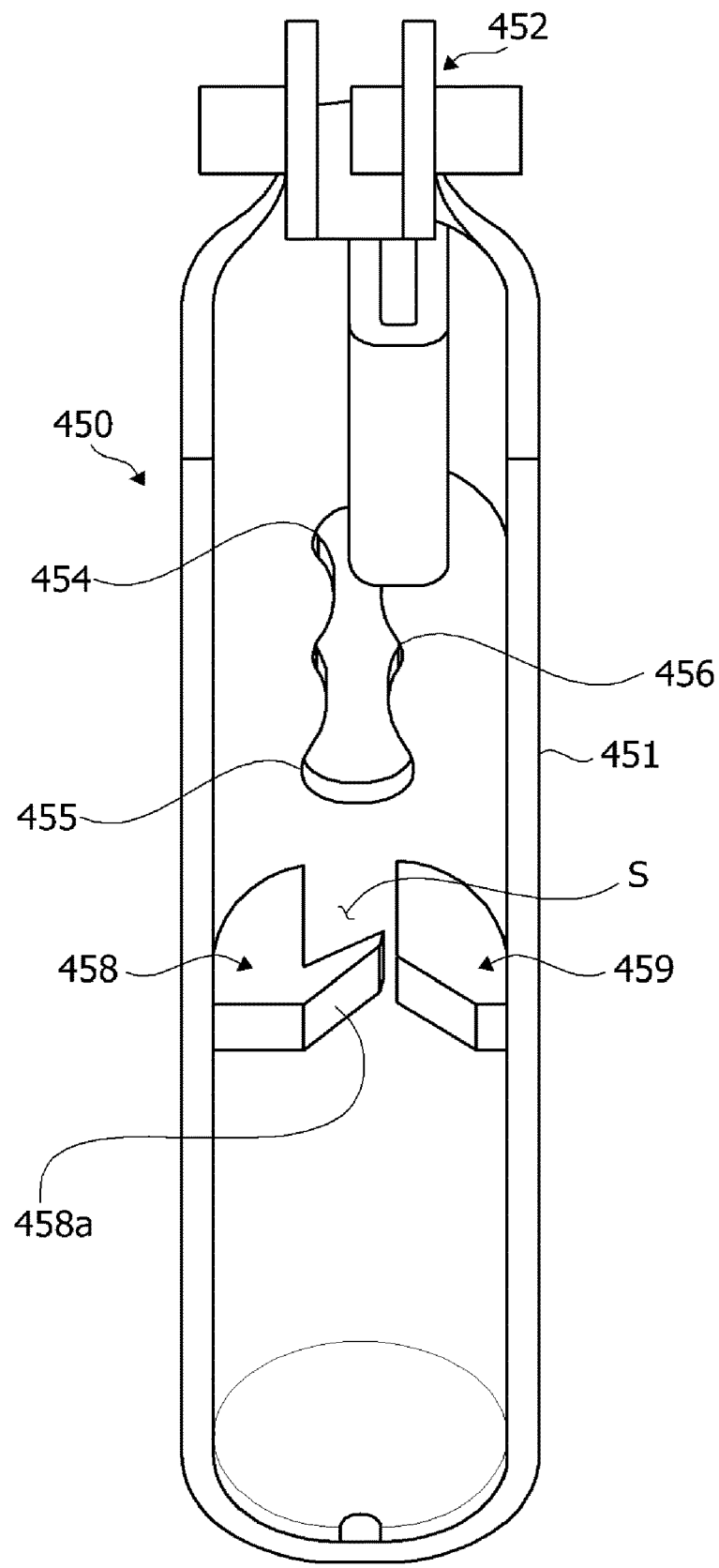
[FIG. 8]

[FIG. 9]
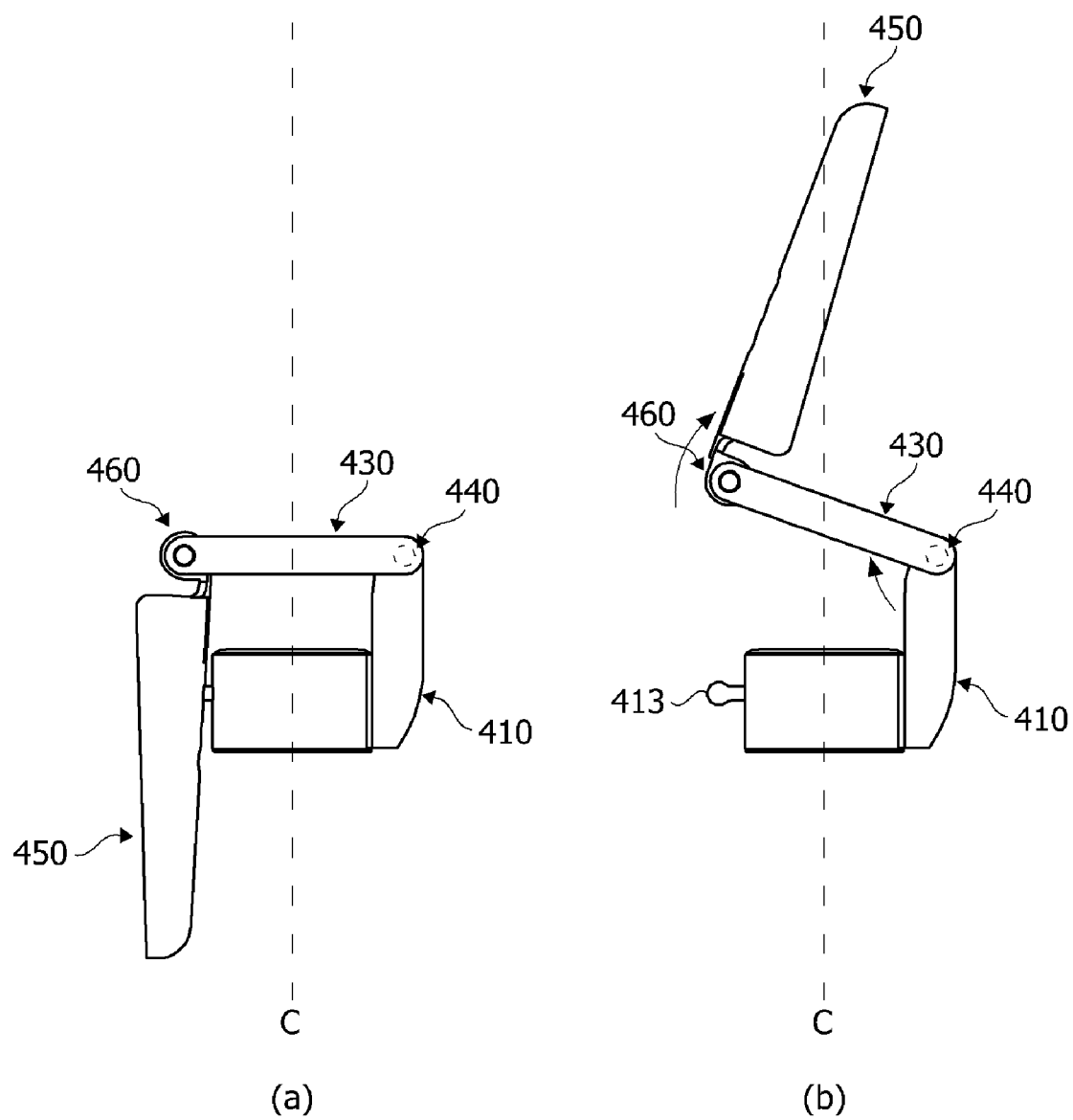
(a)　　　　　　　　　　(b)

[FIG. 10]
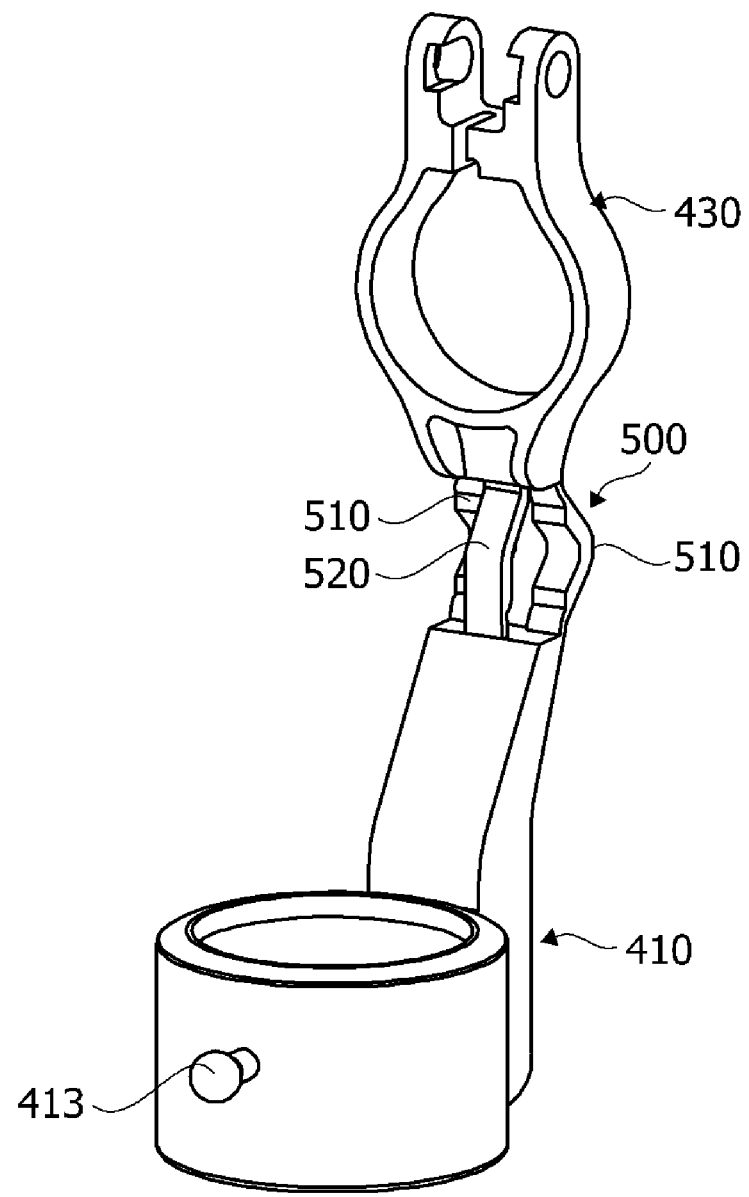

[FIG. 11]
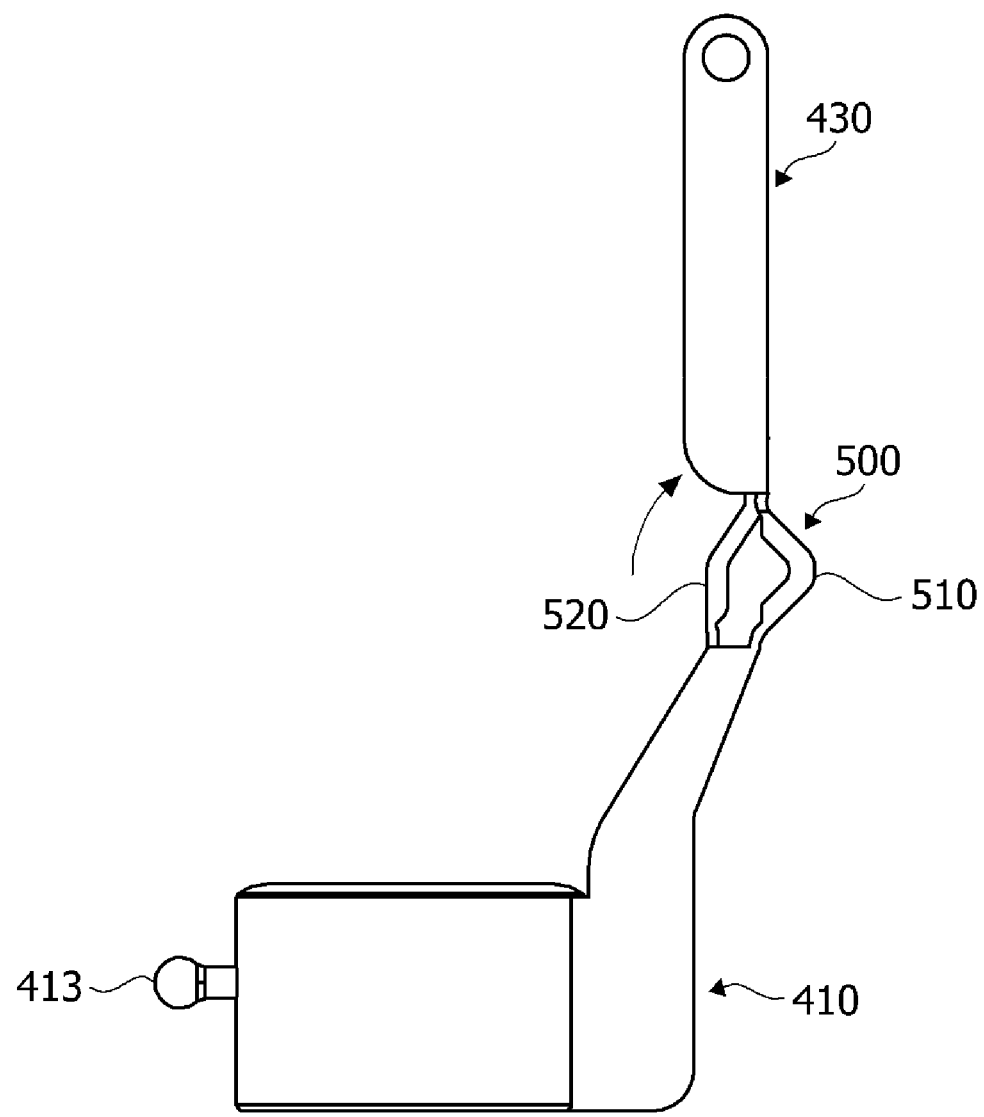

SYRINGE SAFETY CAP AND SAFETY SYRINGE INCLUDING THE SAME

TECHNICAL FIELD

The present disclosure relates to a syringe safety cap and a safety syringe including the same, and more particularly, to a syringe safety cap and a safety syringe including the same capable of safely protecting an injection needle to prevent needlestick injuries.

BACKGROUND

Generally, a syringe includes a cylindrical cylinder having a space formed therein to store an injection solution, a piston moved to absorb or discharge the injection solution from inside the cylinder, a needle holder coupled to a front portion of the cylinder, and a needle coupled to the needle holder.

Meanwhile, securing safety of an injection needle is extremely important. In order to reduce the risk of needlestick injuries that can be fatal in some cases and to prevent reuse of a syringe by a person who misuses a drug so that the probability of drug misuse and the spread of contagious diseases are suppressed, a need has arisen for a disposable syringe and a disposable intravenous infusion set that prevent reuse thereof.

These are also necessary to allow healthcare workers, such as doctors and nurses who provide professional care to patients, to avoid becoming patients themselves due to secondary infection caused by an accidental needlestick injury.

Accordingly, safety syringes that can prevent hospital-acquired infection of healthcare workers have been in use.

Technical Problem

The present disclosure is directed to providing a syringe safety cap and a safety syringe including the same that are capable of safely protecting an injection needle to prevent needlestick injuries and are capable of easy operation.

Technical Solution

One aspect of the present disclosure provides a syringe safety cap including a base portion having a mounting portion to be mounted on a cylinder of a syringe, a link portion rotatably connected to the base portion, a first elastic portion configured to provide a rotational force so that the link portion rotates with respect to the base portion, a safety cover portion rotatably connected to the link portion, detachably fixed to the base portion, and configured to, when detached from the base portion and rotating, surround an injection needle of the syringe, and a second elastic portion configured to provide a rotational force so that the safety cover portion rotates with respect to the link portion.

Another aspect of the present disclosure provides a safety syringe including a cylinder configured to accommodate a medicinal fluid therein, an injection needle provided at one end portion of the cylinder, and the syringe safety cap coupled to the cylinder and provided to selectively cover the injection needle.

Advantageous Effects

A syringe safety cap and a safety syringe including the same relating to at least one embodiment of the present disclosure have the following advantageous effects.

A safety cover portion and a link portion can automatically rotate due to an elastic force provided by a first elastic portion and a second elastic portion just by a simple operation of uncoupling the safety cover portion and a fixing protrusion of a base portion, and the safety cover portion can surround and protect an injection needle.

DESCRIPTION OF DRAWINGS

FIG. 1 is a perspective view illustrating a safety syringe including a syringe safety cap according to an embodiment of the present disclosure.

FIG. 2 is a perspective view illustrating the syringe safety cap according to an embodiment of the present disclosure.

FIG. 3 is an exploded perspective view illustrating the syringe safety cap according to an embodiment of the present disclosure.

FIGS. 4 to 6 are exemplary views illustrating operation examples of the syringe safety cap according to an embodiment of the present disclosure.

FIG. 7 is a lateral view of the syringe safety cap according to an embodiment of the present disclosure.

FIG. 8 is a perspective view of a main portion for describing a coupler of a safety cover portion according to another embodiment.

FIG. 9 is a lateral view for describing an operational state of the syringe safety cap according to an embodiment of the present disclosure.

FIG. 10 is a perspective view of a main portion illustrating a syringe safety cap according to another embodiment of the present disclosure.

FIG. 11 is a lateral view of the syringe safety cap illustrated in FIG. 10.

MODES OF THE INVENTION

Hereinafter, a syringe safety cap and a safety syringe including the same according to an embodiment of the present disclosure will be described in detail with reference to the accompanying drawings.

The present disclosure will be described below with reference to the accompanying drawings. However, the present disclosure may be implemented in various different forms and thus is not limited to the embodiments described herein. Also, parts unrelated to the description have been omitted from the drawings to clearly describe the present disclosure, and like elements are denoted by like reference numerals throughout the specification.

Throughout the specification, when a certain portion is described as being "connected to (linked to, in contact with, coupled to)" another portion, this not only includes a case in which the portion is "directly connected" to the other portion but also includes a case in which the portion is "indirectly connected" to the other portion while another constituent member is disposed therebetween.

FIG. 1 is a perspective view illustrating a safety syringe including a syringe safety cap according to an embodiment of the present disclosure, FIG. 2 is a perspective view illustrating the syringe safety cap according to an embodiment of the present disclosure, and FIG. 3 is an exploded perspective view illustrating the syringe safety cap according to an embodiment of the present disclosure.

Also, FIG. 7 is a lateral view of the syringe safety cap according to an embodiment of the present disclosure, FIG. 8 is a perspective view of a main portion for describing a coupler of a safety cover portion according to another embodiment, and FIG. 9 is a lateral view for describing an operational state of the syringe safety cap according to an embodiment of the present disclosure.

As illustrated in FIGS. 1 to 3, a safety syringe (also abbreviated as "syringe") may include a cylinder 200, an injection needle 300, and a syringe safety cap 400.

The cylinder 200 may form a main body of the safety syringe and accommodate a medicinal fluid or accommodate different medicines or liquid medicines therein. When two or more types of medicines or liquid medicines are accommodated in the cylinder 200, at least two or more rubber stoppers may be arranged inside the cylinder 200, and different medicines or liquid medicines may be accommodated in separate accommodation spaces in the cylinder that are isolated by the stoppers.

The injection needle 300 may be provided at one end portion of the cylinder 200. Here, a needle holder 301 may be further provided at the one end portion of the cylinder 200, and the injection needle 300 may be coupled to the needle holder 301. That is, the injection needle 300 may be fixed to the needle holder 301, and the needle holder 301 may be mounted on the cylinder 200.

Also, a plunger rod may be coupled to the other end portion of the cylinder. A user may press the plunger rod toward the injection needle 300 to discharge a medicinal fluid, which is in the accommodation space in the cylinder, to the outside through the injection needle 300.

Also, the syringe safety cap 400 may be coupled to the cylinder 200. For example, the syringe safety cap 400 may be coupled to the one end portion of the cylinder that is adjacent to the injection needle 300. The syringe safety cap 400 may selectively cover the injection needle 300 and, in this way, prevent a needlestick injury caused by the injection needle 300. For example, the syringe safety cap 400 may also be fitted and coupled to the cylinder 200 or heat-bonded to the cylinder 200.

Also, the syringe safety cap 400 relating to an embodiment (first embodiment) of the present disclosure may include a base portion 410, a link portion 430, a first elastic portion 440, a safety cover portion 450, and a second elastic portion 460.

Specifically, the syringe safety cap 400 includes the base portion 410 having a mounting portion to be mounted on the cylinder 200 of the syringe, the link portion 430 rotatably connected to the base portion 410, and the first elastic portion 440 configured to provide a rotational force so that the link portion 430 rotates with respect to the base portion 410.

Also, the syringe safety cap 400 includes the safety cover portion 450 rotatably connected to the link portion 430, detachably fixed to the base portion 410, and configured to, when detached from the base portion 410 and rotating, surround the injection needle 300 of the syringe, and the second elastic portion 460 configured to provide a rotational force so that the safety cover portion 450 rotates with respect to the link portion 430.

First, the base portion 410 may be coupled to the one end portion of the cylinder 200 having a medicinal fluid accommodated therein.

Also, the link portion 430 may be axially coupled (or connected) to the base portion 410. In the present document, being "axially coupled (or connected)" refers to being coupled (connected) to be rotatable about a predetermined axis of rotation. For example, the syringe safety cap may have a first axial portion configured to provide a center of rotation of the link portion 430 with respect to the base portion 410. Also, the first axial portion may include the first elastic portion 440 described above.

Here, the first axial portion may include a first rotating shaft 434 and a first coupling hole 417 mounted to allow rotation of the first rotating shaft 434. Specifically, the link portion 430 may include any one of the first rotating shaft 434 and the first coupling hole 417 constituting the first axial portion, and the base portion 410 may include the other one of the first rotating shaft 434 and the first coupling hole 417 constituting the first axial portion. For example, referring to FIG. 3, the link portion 430 may include the first rotating shaft 434 and the base portion 410 may include the first coupling hole 417, but the present disclosure is not limited thereto, and the opposite is also possible.

Also, the safety cover portion 450 may be axially coupled (or connected) to the link portion 430. The syringe safety cap may have a second axial portion configured to provide a center of rotation of the safety cover portion 450 with respect to the link portion 430. Also, the second axial portion may include the second elastic portion 460 described above.

Here, the second axial portion may include a second rotating shaft 452 and a second coupling hole 433 mounted to allow rotation of the second rotating shaft 452. Specifically, the link portion 430 may include any one of the second rotating shaft 452 and the second coupling hole 433 constituting the second axial portion, and the safety cover portion 450 may include the other one of the second rotating shaft 452 and the second coupling hole 433 constituting the second axial portion. For example, referring to FIG. 3, the safety cover portion 450 may include the second rotating shaft 452 and the link portion 430 may include the second coupling hole 433, but the present disclosure is not limited thereto, and the opposite is also possible.

Also, the injection needle 300 of the syringe may be located between the first axial portion, which provides the center of rotation of the link portion 430 with respect to the base portion 410, and the second axial portion, which provides the center of rotation of the safety cover portion with respect to the link portion 430. That is, the injection needle 300 may be located between the first axial portion and the second axial portion.

For example, the first axial portion may be located at one end portion of the link portion 430, and the second axial portion may be located at the other end portion thereof. Also, in a state in which the safety cover portion 450 is fixed to the base portion 410, the link portion 430 may be disposed to surround a partial area of the cylinder 200. Also, in a process in which the safety cover portion 450 is detached from the base portion 410 and surrounds the injection needle 300, the safety cover portion 450 may break away from the cylinder 200 of the syringe.

Meanwhile, in the process in which the safety cover portion 450 surrounds the injection needle, the second axial portion may be moved to approach the injection needle 200 of the syringe. Unlike this, the first axial portion may be provided so that a change in the position thereof does not occur in the process in which the safety cover portion 450 surrounds the injection needle.

Also, the first axial portion, which provides the center of rotation of the link portion 430 with respect to the base portion 410, and the second axial portion, which provides the center of rotation of the safety cover portion 450 with respect to the link portion 430, may be arranged to be parallel. Meanwhile, the first axial portion and the second axial portion may each be provided so that the axis of the center of rotation thereof is perpendicular to a direction of a central axis C of the cylinder. In the present document, the reference sign "C" indicates the central axis of the cylinder, and the central axis of the cylinder may be coaxial with the injection needle 300.

Also, in the process in which the safety cover portion 450 surrounds the injection needle 300, a direction of rotation of the link portion 430 with respect to the base portion 410 and a direction of rotation of the safety cover portion 450 with respect to the link portion 430 may be provided to be the same. That is, in the process in which the safety cover portion 450 surrounds the injection needle 300, rotation about the first axial portion and rotation about the second axial portion may be performed in the same direction (for example, a first direction of rotation).

Also, in the process in which the safety cover portion 450 is detached (or uncoupled) from the base portion 410 and surrounds the injection needle 300, an angle of rotation of the link portion 430 with respect to the base portion 410 may be provided to be smaller than an angle of rotation of the safety cover portion 450 with respect to the link portion 430. That is, the safety cover portion 450 may rotate about a larger angle as compared to rotation of the link portion 430 with respect to the base portion 410.

Also, the first elastic portion 440 interposed in the first axial portion and the second elastic portion 460 interposed in the second axial portion may each include a spring (for example, a torsion spring).

As described above, referring to FIG. 3, the link portion 430 may have one end portion rotatably coupled to the base portion 410 through the first rotating shaft 434, and when the link portion 430 rotates in a first direction of rotation R1 (see FIG. 5) about the first rotating shaft 434, the link portion 430 may be moved to an outer side of the one end portion of the cylinder 200.

The first elastic portion 440 may be mounted on the first rotating shaft 434 and may provide an elastic force so that the link portion 430 rotates in the first direction of rotation R1 (see FIG. 5).

Also, the safety cover portion 450 may have one end portion rotatably coupled to the link portion 430 through the second rotating shaft 452 and may rotate in the first direction of rotation R1 (see FIG. 5) about the second rotating shaft 452 and cover the injection needle 300. That is, the first direction of rotation R1 may be a direction in which the safety cover portion 450 is uncoupled from the base portion 410 and in which the link portion 430 and the safety cover portion 450 are unfolded.

Also, the second elastic portion 460 may be mounted on the second rotating shaft 452 and may provide an elastic force so that the safety cover portion 450 rotates in the first direction of rotation R1 (see FIG. 5).

Therefore, in a state in which the safety cover portion 450 is coupled to the base portion 410, when a force is applied from the outside to uncouple the safety cover portion 450 and the base portion 410, the safety cover portion 450 rotates in the first direction of rotation R1 (see FIG. 5) due to the elastic force generated by the second elastic portion 460, and simultaneously, the link portion 430 rotates in the first direction of rotation R1 (see FIG. 5) due to the elastic force generated by the first elastic portion 440.

That is, just by one operation in which a user uncouples the safety cover portion 450 and the base portion 410, the safety cover portion 450 may be operated to cover the injection needle 300, and in this way, the safety cover portion 450 may protect the injection needle 300 and prevent a needlestick injury.

Referring to FIG. 3, the base portion 410 may have a coupling ring 411, a first extension bar 412, and a fixing protrusion 413. The base portion 410 may be made of, for example, a resin material.

The base portion 410 may include the coupling ring 411 configured to provide a mounting portion coupled while surrounding an outer circumferential surface of the cylinder of the syringe in a circumferential direction, the first extension bar 412 connected to the coupling ring 411, formed to extend in a longitudinal direction (or a direction of a central axis) of the cylinder 200 of the syringe, and having any one of the first rotating shaft and the first coupling hole, which constitute the first axial portion, formed therein, and the fixing protrusion 413 provided on the coupling ring 411 and provided to be detachably coupled to the safety cover portion 450.

Specifically, the coupling ring 411 may be coupled while surrounding the outer circumferential surface of the one end portion of the cylinder 200 in the circumferential direction.

Also, the first extension bar 412 may be connected to the coupling ring 411 and formed to extend toward the one end portion of the cylinder 200. Also, the first extension bar 412 may be provided as a pair of first extension bars 412 located to be spaced apart at a predetermined interval. Also, a pair of first coupling holes 417 may be formed to be symmetrical to each other in the first extension bars 412.

Meanwhile, the fixing protrusion 413 may have a column 414 and a stopper 415.

The column 414 may be formed to protrude from the coupling ring 411 in a radial direction of the cylinder 200 of the syringe. The column 414 may have a first diameter D1.

The stopper 415 may be formed on an upper end portion of the column 414 and have a second diameter D2. The second diameter D2 may be larger than the first diameter D1.

Also, the link portion 430 may have a link body 431 and a second extension bar 432. The link portion 430 may be made of, for example, a resin material.

Also, the link portion 430 may include the link body 431, which is formed to surround the outer circumferential surface of the cylinder 200 of the syringe in a state in which the safety cover portion 450 is fixed to the base portion 410 and which has one of the second rotating shaft 452 and the second coupling hole 433 which constitute the second axial portion, and the second extension bar, which is connected to the link body 431 and has the other one of the first rotating shaft 434 and the first coupling hole 417 which constitute the first axial portion.

FIG. 3 illustrates an embodiment in which the second coupling hole 433 is provided in the link body 431 and the first rotating shaft 434 is provided on the second extension bar.

Referring to FIGS. 2 and 3, the link body 431 may be formed to surround an outer circumferential surface of a stepped portion 201 formed on the one end portion of the cylinder 200.

Also, both end portions of the link body 431 may be formed to be spaced apart from each other and formed to extend to an outer side of the cylinder 200. Referring to FIG. 3, a pair of second coupling holes 433 may be formed in both end portions of the link body 431.

The second extension bar 432 may be connected to the link body 431 and extend in a direction perpendicular to the longitudinal direction of the cylinder 200.

A pair of second extension bars 432 may be formed to be spaced apart at a predetermined interval, and referring to FIG. 3, the first rotating shaft 434 may be formed on one end portion of the second extension bar 432.

Also, the first extension bar 412 of the base portion 410 may be inserted between the second extension bars 432, and the first rotating shaft 434 may be coupled to the first coupling hole 417. As a result, the link portion 430 may rotate about the first rotating shaft 434.

The first rotating shaft 434 may be formed to be perpendicular to the longitudinal direction (or the direction of the central axis) of the cylinder 200.

The first elastic portion 440 may be coupled to the first shaft 434. For example, the first elastic portion 440 may be a coil spring or a torsion spring and may provide an elastic force so that the link portion 430 rotates in the first direction of rotation R1 (see FIG. 5) about the first rotating shaft 434.

Here, when the link portion 430 rotates in the first direction of rotation R1 (see FIG. 5) about the first rotating shaft 434, the link body 431 may be moved to an outer side of one end portion of the base portion 410. Also, when the link portion 430 rotates in a second direction of rotation, which is the opposite direction of the first direction of rotation R1 (see FIG. 5) about the first rotating shaft 434, the link body 431 may be located on the stepped portion 201 formed on the one end portion of the cylinder 200, and the stepped portion 201 may be located at an inner side of the link body 431. The second direction of rotation may be a direction in which the link portion 430 and the safety cover portion 450 are folded so that the safety cover portion 450 is fixed to the base portion 410.

Meanwhile, the safety cover portion 450 may include a cover body 451 in which the injection needle 300 of the syringe is accommodated and the other one of the second rotating shaft 452 and the second coupling hole 433 which constitute the second axial portion is provided (in the embodiment illustrated in FIG. 3, the second rotating shaft is provided). Also, the cover body 451 of the safety cover portion 450 may have a coupling slit 454 formed to extend through the cover body 451 in a longitudinal direction thereof to be coupled to the fixing protrusion 413. The safety cover portion 450 may be made of, for example, a resin material.

The cover body 451 may be concavely formed so that the injection needle 300 is accommodated therein, and the second rotating shaft 452 may be provided on one end portion of the cover body 451. The second rotating shaft 452 may be provided as a pair of second rotating shafts 452 symmetrical to each other. Also, the cover body 451 may have a flat shape instead of being inclined in the longitudinal direction thereof.

Referring to the embodiment illustrated in FIG. 3, the second rotating shaft 452 may be coupled to the second coupling hole 433 of the link portion 430. The second rotating shaft 452 may be formed to be perpendicular to the longitudinal direction (or the direction of the central axis) of the cylinder 200.

The coupling slit 454 may be formed to pass through the center of the cover body 451 and formed to extend in the longitudinal direction of the cover body 451.

When rotation of the safety cover portion 450 in the second direction of rotation, which is the opposite direction of the first direction of rotation, is completed and the cover body 451 is pressed against the coupling ring 411, the fixing protrusion 413 may be inserted into and coupled to the coupling slit 454.

A width W of at least a partial area of the coupling slit 454 may be formed to be smaller than the first diameter D1 of the column 414 of the fixing protrusion 413. Preferably, the width W of at least a partial area of the coupling slit 454 may be formed to be slightly smaller than the first diameter D1.

Also, the coupling slit 454 may have a first insertion groove 455 and a second insertion groove 456.

The first insertion groove 455 may be formed in one end portion of the coupling slit 454. The first insertion groove 455 may be formed to have a third diameter D3, which is larger than the second diameter D2 of the stopper 415 of the base portion 410, so that the stopper 415 is insertable into the first insertion groove 455. Therefore, the stopper 415 may be inserted into the first insertion groove 455.

Also, the second insertion groove 456 may be formed in a central portion of the coupling slit 454. The second insertion groove 456 may be formed to have a fourth diameter D4 which is larger than the first diameter D1 of the column 414 and smaller than the second diameter D2 of the stopper 415.

Accordingly, when the safety cover portion 450 moves along the cylinder 200 (for example, moves toward the other end portion thereof) in a state in which the stopper 415 of the fixing protrusion 413 is inserted into the first insertion groove 455, the column 414 may be moved along the coupling slit 454 and inserted into the second insertion groove 456.

Here, although the width W of at least a partial area of the coupling slit 454 is smaller than the first diameter D1 of the column 414, as the coupling slit 454 widens due to the column 414 when the safety cover portion 450 moves toward the other end portion of the cylinder 200, the column 414 may be inserted into the second insertion groove 456. The column 414 inserted into the second insertion groove 456 may be fixed to the second insertion groove 456 unless a separate extremal force is applied thereto.

Then, when an external force is applied to the safety cover portion 450 causing the safety cover portion 450 to move toward the one end portion of the cylinder 200, the column 414 may be moved to the first insertion groove 455 along the coupling slit 454, and when the safety cover portion 450 rotates in the first direction of rotation R1 about the second rotating shaft 452, the stopper 415 may exit the first insertion groove 455, and the safety cover portion 450 and the fixing protrusion 413 are uncoupled.

The second elastic portion 460 may be coupled to the second shaft 452. The second elastic portion 460 may be a coil spring or a torsion spring and may provide an elastic force so that the safety cover portion 450 rotates in the first direction of rotation R1 (see FIG. 5) about the second rotating shaft 452.

When the safety cover portion 450 rotates in the first direction of rotation R1 (see FIG. 5) about the second rotating shaft 452, as the safety cover portion 450 rotates toward the injection needle 300, the injection needle 300 may be accommodated in the cover body 451.

The cover body 451 may have a wing portion 451a formed at both side edges in the longitudinal direction to sufficiently cover the injection needle 300 when rotation of the cover body 451 is completed. Referring to FIG. 7, the wing portion 451a may be provided to, in a state in which the cover body 451 is fixed to the base portion 410, further protrude in the radial direction of the cylinder with respect to a virtual line segment L that is parallel to the central axis C of the cylinder.

The safety cover portion 450 may have a coupler 457 into which a partial area of the injection needle 300 is inserted when rotation of the safety cover portion 450 is completed and the safety cover portion 450 surrounds the injection needle 300. Also, one end portion of the coupler 457 may be formed to be spaced apart from an inner circumferential surface of the cover body 451. Accordingly, a separation portion 457a may be formed between the one end portion of the coupler 457 and the inner circumferential surface of the cover body 451.

When rotation of the cover body 451 in the first direction of rotation R1 about the second rotating shaft 452 is completed and the cover body 451 covers the injection needle 300, the injection needle 300 may be accommodated in the cover body 451, and one end portion of the injection needle 300 may be inserted into the coupler 457 through the separation portion 457a and coupled to the coupler 457.

Referring to FIG. 8, the coupler may include a first protruding portion 458 and a second protruding portion 459 that are located to be spaced apart to form an accommodation space S for the injection needle 300. Here, the coupler is provided to allow the injection needle 300 to be inserted into the space between the first protruding portion 458 and the second protruding portion 459, and a catching protrusion 458a configured to prevent the injection needle 300 from breaking away is provided on the first protruding portion 458. Of course, a predetermined space is provided between the catching protrusion 458a and the second protruding portion 459, and the space is formed to have a width narrower than that of the accommodation space S. Also, an inclined surface may be provided on an inlet side of the injection needle 300 on each of the catching protrusion 458a and the second protruding portion 459.

Hereinafter, an operation of the syringe safety cap will be described.

FIGS. 4 to 6 are exemplary views illustrating operation examples of the syringe safety cap according to an embodiment of the present disclosure.

First, as illustrated in FIG. 4A, before the syringe is used, the injection needle 30 may be covered with a needle cap 10.

The syringe safety cap 400 may not interfere with the needle cap 10 being coupled to the one end portion of the cylinder 200.

In a state in which the needle cap 10 is coupled, the link portion 430 of the syringe safety cap 400 may be in a state of, after rotation thereof in the second direction of rotation is completed, being located to surround the outer circumferential surface of the stepped portion 201 of the cylinder 200, and the safety cover portion 450 may also be in a state of, after rotation thereof in the second direction of rotation is completed, being coupled and bound to the fixing protrusion 413 of the base portion 410. Accordingly, the safety cover portion 450 and the link portion 430 may be fixed so as not to be rotated in the first direction of rotation R1.

Also, as illustrated in FIG. 4B, the needle cap 10 may be removed before using the syringe. A user may lightly push up the needle cap 10 to remove the needle cap 10. After removing the needle cap 10, the user may give an injection to a patient or the like.

Meanwhile, in a state in which use of the syringe is completed, the column 414 of the fixing protrusion 413 may be in a state of being inserted into the second insertion groove 456. In this state, when the user pushes the safety cover portion 450 upward as illustrated in FIG. 5A, as illustrated in FIG. 5B, the column 414 of the fixing protrusion 413 is moved along the coupling slit 454 and moved to the first insertion groove 455, and the link portion 430 rotates in the first direction of rotation R1 about the first rotating shaft 434.

Then, in this state, when the user lifts the safety cover portion 450 and the stopper 415 exits the first insertion groove 455, the safety cover portion 450 rotates in the first direction of rotation R1 due to the elastic force provided by the second elastic portion 460. Also, simultaneously, the link portion 430 rotates in the first direction of rotation R1 due to the elastic force provided by the first elastic portion 440.

Then, as illustrated in FIG. 6, the link body 431 of the link portion 430 may be moved to the outer side of the stepped portion 201 about the first rotating shaft 434, and the second rotating shaft 452 may be moved to an upper side of the cylinder 200. Also, the safety cover portion 450 may rotate about the second rotating shaft 452, and an upper end portion of the safety cover portion 450 may be moved to the upper side of the cylinder 200.

That is, the safety cover portion 450 and the link portion 430 may be unfolded due to moving to the upper side of the cylinder 200, and the injection needle 300 may be accommodated in the cover body 451.

Also, one end portion of the injection needle 300 may be inserted and coupled to the coupler 457 of the safety cover portion 450, and in this way, unintentional separation between the safety cover portion 450 and the injection needle 300 may be prevented.

In this way, according to the present disclosure, just by a simple operation of releasing a coupling force between the fixing protrusion 413 and the safety cover portion 450, the safety cover portion 450 and the link portion 430 may simultaneously and automatically rotate due to the elastic force provided by the first elastic portion 440 and the second elastic portion 460, and the safety cover portion 450 may cover the injection needle 300.

FIG. 10 is a perspective view of a main portion illustrating a syringe safety cap according to another embodiment (second embodiment) of the present disclosure, and FIG. 11 is a lateral view of the syringe safety cap illustrated in FIG. 10.

Referring to FIGS. 10 and 11, the syringe safety cap according to the second embodiment is different from the syringe safety cap according to the first embodiment only in terms of configurations of a first elastic portion and a first axial portion, and all other elements are the same. Hereinafter, only the configurations different from the first embodiment will be described in detail.

Specifically, a first elastic portion 500 includes one or more bridges 510 and 520 which connect the link portion 430 and the base portion 410 and in which at least a partial area is bent. In the second embodiment, rotation of the link portion 430 with respect to the base portion 410 uses a rotational force using the bent shape of the bridges.

Also, a second elastic portion includes a spring as in the first embodiment.

Specifically, the bridges may include the first bridge 510 and the second bridge 520 which are bent in the opposite directions. The first bridge and the second bridge may be bent in a substantially "V" shape.

Also, an angle at which the first bridge 510 is bent and an angle at which the second bridge 520 is bent may be different. Also, the number of first bridges 510 and the number of second bridges 520 may be different. For example, the first elastic portion 500 may include a pair of first bridges 510, and the second bridge 520 may be disposed between the pair of first bridges 510.

Also, in the second embodiment, the first axial portion may consist of one or more bridges connecting the link portion 430 and the base portion 410 instead of consisting of a rotating shaft and a coupling hole.

The exemplary embodiments of the present disclosure which have been described above are only disclosed for an illustrative purpose, and those of ordinary skill in the art should be able to make various modifications, changes, and additions within the idea and scope of the present disclosure, and such modifications, changes, and additions should be construed as falling within the scope of the claims below.

INDUSTRIAL APPLICABILITY

According to a syringe safety cap and a safety syringe including the same relating to at least one embodiment of the present disclosure, just by a simple operation of uncoupling a safety cover portion and a fixing protrusion of a base portion, an injection needle can be surrounded and protected by the safety cover portion.

The invention claimed is:

1. A syringe safety cap comprising:
a base portion having a mounting portion to be mounted on a cylinder of a syringe;
a link portion rotatably connected to the base portion;
a first elastic portion configured to provide a rotational force so that the link portion rotates with respect to the base portion;
a safety cover portion rotatably connected to the link portion, detachably fixed to the base portion, and configured to, when detached from the base portion and rotating, surround an injection needle of the syringe; and
a second elastic portion configured to provide a rotational force so that the safety cover portion rotates with respect to the link portion,
wherein the injection needle of the syringe is located between a first axial portion configured to provide a center of rotation of the link portion with respect to the base portion and a second axial portion configured to provide a center of rotation of the safety cover portion with respect to the link portion, and
wherein, in a process in which the safety cover portion surrounds the injection needle, a direction of rotation of the link portion with respect to the base portion and a direction of rotation of the safety cover portion with respect to the link portion are provided to be the same.

2. The syringe safety cap of claim 1, wherein, in a process in which the safety cover portion surrounds the injection needle, the second axial portion is moved to approach the injection needle of the syringe.

3. The syringe safety cap of claim 1, wherein the first axial portion configured to provide the center of rotation of the link portion with respect to the base portion and the second axial portion configured to provide the center of rotation of the safety cover portion with respect to the link portion are arranged to be parallel.

4. The syringe safety cap of claim 1, wherein, in a process in which the safety cover portion surrounds the injection needle, an angle of rotation of the link portion with respect to the base portion is provided to be smaller than an angle of rotation of the safety cover portion with respect to the link portion.

5. The syringe safety cap of claim 1, wherein the link portion is disposed to surround the cylinder of the syringe in a state in which the safety cover portion is fixed to the base portion, and the link portion breaks away from the cylinder of the syringe in a process in which the safety cover portion surrounds the injection needle.

6. The syringe safety cap of claim 1, wherein the first elastic portion and the second elastic portion each include a spring.

7. The syringe safety cap of claim 1, wherein:
the first elastic portion includes one or more bridges which connect the link portion and the base portion and in which at least a partial area is bent; and
the second elastic portion includes a spring.

8. The syringe safety cap of claim 7, wherein the bridges include a first bridge and a second bridge which are bent in opposite directions.

9. The syringe safety cap of claim 8, wherein an angle at which the first bridge is bent and an angle at which the second bridge is bent are different.

10. The syringe safety cap of claim 1, wherein the base portion includes:
a coupling ring configured to provide a mounting portion coupled while surrounding an outer circumferential surface of the cylinder of the syringe in a circumferential direction;
a first extension bar connected to the coupling ring, formed to extend in a longitudinal direction of the cylinder of the syringe, and having any one of a first rotating shaft and a first coupling hole, which constitute the first axial portion, formed therein; and
a fixing protrusion provided on the coupling ring and provided to be detachably coupled to the safety cover portion.

11. The syringe safety cap of claim 10, wherein the fixing protrusion includes a column which is formed to protrude in a radial direction of the cylinder of the syringe and has a first diameter and a stopper which is formed on an upper end portion of the column and has a second diameter larger than the first diameter.

12. The syringe safety cap of claim 11, wherein the link portion includes a link body, which is formed to surround an outer circumferential surface of the cylinder of the syringe in a state in which the safety cover portion is fixed to the base portion and which has one of a second rotating shaft and a second coupling hole which constitute the second axial portion, and a second extension bar, which is connected to the link body and has the other one of the first rotating shaft and the first coupling hole which constitute the first axial portion.

13. The syringe safety cap of claim 12, wherein:
the safety cover portion includes a cover body in which the injection needle of the syringe is accommodated and the other one of the second rotating shaft and the second coupling hole which constitute the second axial portion is provided; and
the cover body has a coupling slit formed to extend through the cover body in a longitudinal direction thereof to be coupled to the fixing protrusion.

14. The syringe safety cap of claim 13, wherein the coupling slit includes a first insertion groove having a third diameter, which is larger than the second diameter, so that the stopper is inserted into the first insertion groove and a second insertion groove formed in a central portion of the coupling slit and having a fourth diameter, which is larger than the first diameter and smaller than the second diameter, so that the column is inserted into and fixed to the second insertion groove when the safety cover portion moves along the cylinder in a state in which the stopper is inserted into the first insertion groove.

15. The syringe safety cap of claim 1, wherein the safety cover portion has a coupler into which a partial area of the injection needle is inserted when rotation of the safety cover portion is completed and the safety cover portion surrounds the injection needle.

16. The syringe safety cap of claim 2, wherein the first axial portion and the second axial portion are each provided so that the axis of the center of rotation thereof is perpendicular to a direction of a central axis of the cylinder.

17. A safety syringe comprising:
a cylinder configured to accommodate a medicinal fluid therein;
an injection needle provided at one end portion of the cylinder; and
the syringe safety cap of any one of claims 1, 2, 3 and 4 to 16 that is coupled to the cylinder and provided to selectively cover the injection needle.

\* \* \* \* \*